US00PP15020P3

(12) United States Plant Patent
Weeks

(10) Patent No.: US PP15,020 P2
(45) Date of Patent: Jul. 13, 2004

(54) HYBRID TEA ROSE PLANT NAMED 'WEZAPRT'

(50) Latin Name: *Rosa hybrida*
Varietal Denomination: Wezaprt

(75) Inventor: O. L. Weeks, Chino, CA (US)

(73) Assignee: CP Delaware, Inc., Wilmington, DE (US)

( * ) Notice: Subject to any disclaimer, the term of this patent is extended or adjusted under 35 U.S.C. 154(b) by 6 days.

(21) Appl. No.: 10/383,576

(22) Filed: Mar. 10, 2003

(65) Prior Publication Data

US 2003/0167546 P1 Sep. 4, 2003

Related U.S. Application Data

(63) Continuation of application No. 10/160,192, filed on Jun. 4, 2002, now abandoned, which is a continuation of application No. 09/756,735, filed on Jan. 10, 2001, now abandoned.

(51) Int. Cl.[7] ..... A01H 5/00

(52) U.S. Cl. ..... Plt./130

(58) Field of Search ..... Plt./130

*Primary Examiner*—Anne Marie Grunberg
*Assistant Examiner*—Susan B. McCormick-Ewoldt
(74) *Attorney, Agent, or Firm*—Burns, Doane, Swecker & Mathis, L.L.P.

(57) ABSTRACT

A new and distinct variety of Hybrid Tea rose plant is provided which forms attractive large double blossoms with a spicy fragrance that are amber-orange in coloration. The plant exhibits a bushy, vigorous and uniform growth habit, medium green foliage, and good tolerance to rose black spot. The attractive medium green foliage contrasts nicely with the lighter-colored blossoms. The new variety is particularly well suited for growing as attractive ornamentation in the landscape such as in parks and gardens. Cut flower production also is possible.

11 Drawing Sheets

Figure 1:
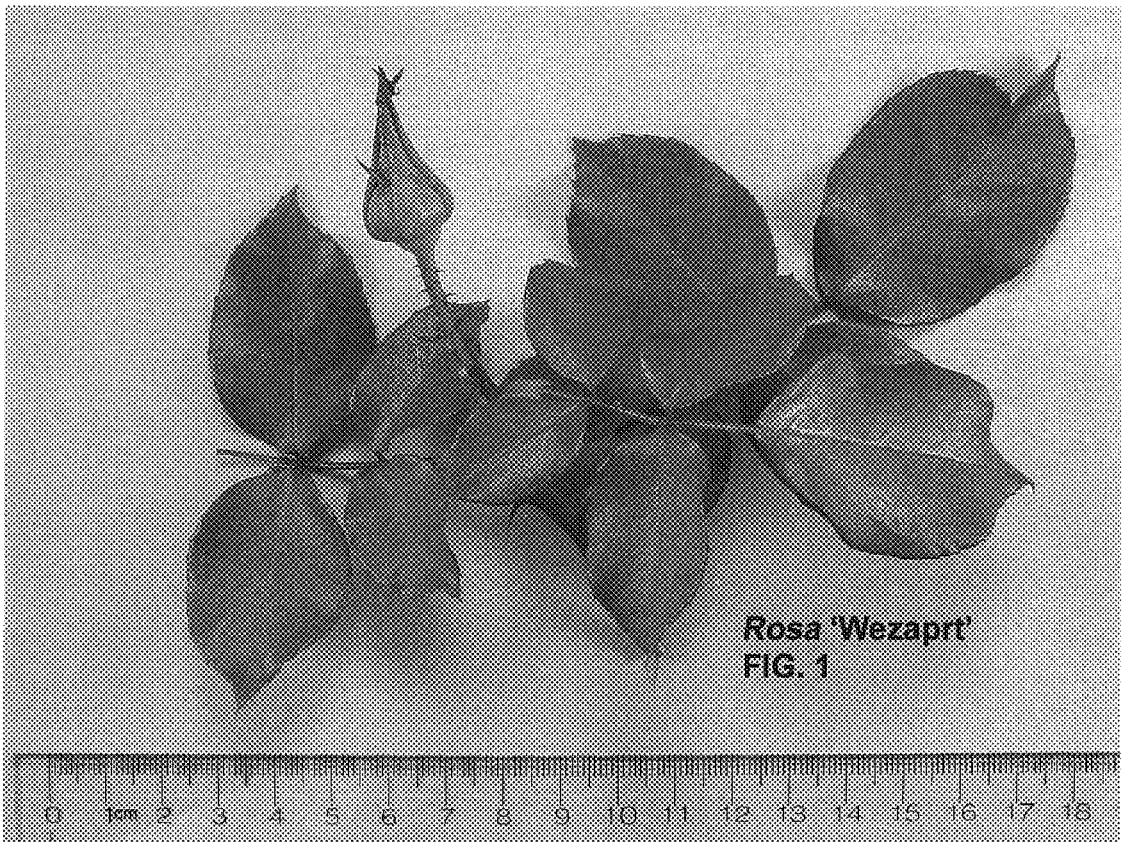

Botanical/commercial classification: Rosa hybrida/Hybrid Tea Rose Plant.

Varietal denomination: cv. 'Wezaprt'.

This is a Continuation of U.S. Plant application Ser. No. 10/160,192, filed Jun. 4, 2002, which is a Continuation of U.S. Plant patent application Ser. No. 09/756,735, filed Jan. 10, 2001, now abandoned.

SUMMARY OF THE INVENTION

The new variety of Rosa hybrida Hybrid Tea rose plant was created by artificial pollination wherein two parents were crossed which previously had been studied in the hope that they would contribute the desired characteristics. The female parent (i.e., the seed parent) of the new variety was the 'Just Joey' variety (non-patented in the United States). The male parent (i.e., the pollen parent) was an unnamed seedling (non-patented in the United States). The parentage of the new variety can be summarized as follows:

'Just Joey'×Unnamed Seedling.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) exhibits a bushy, vigorous and uniform growth habit, (b) forms attractive large double blossoms with a spicy fragrance that are amber-orange in coloration, (c) forms medium green semi-glossy foliage that contrasts well with the lighter-colored blossoms, (d) exhibits good disease tolerance to rose black spot, and (e) is particularly well suited for growing as attractive ornamentation.

The new variety well meets the needs of the horticultural industry and can be grown to advantage for cut flower production, as a specimen plant, or in a mass planting.

The new variety of the present invention can be readily distinguished from previously known varieties. For instance, the 'Just Joey' female parent forms high centered buds, and smaller flowers with more petals that assume pink tones upon full maturity. No information is available concerning the specific ways in which the new variety differs from the male parent since such parent is not available for observation and there are no known records concerning its characteristics.

The new variety has been found to undergo asexual propagation by budding, and grafting. Asexual propagation by these techniques at West Grove, Pa. and at Wasco, Calif. has shown that the characteristics of the new variety are stable and are strictly transmissible by such asexual propagation from one generation to another.

The asexual reproduction of the new variety by the rooting of cuttings is not known to have been conducted. However, it is anticipated that a semi-hardwood cutting would root under commercial conditions in approximately three weeks.

The new variety has been named the 'Wezaprt' variety. The new variety is being marketed under the BRONZE STAR trademark.

BRIEF DESCRIPTION OF THE PHOTOGRAPHS

The accompanying photographs show as nearly true as it is reasonably possible to make the same, in color illustrations of this character, typical specimens of the plant parts of the new variety. The rose plants of the new variety were two years of age and were observed during September 2003 while growing on 'Dr. Huey' rootstock at Wasco, Calif. Dimensions in centimeters are indicated in each photograph.

Figure 2:
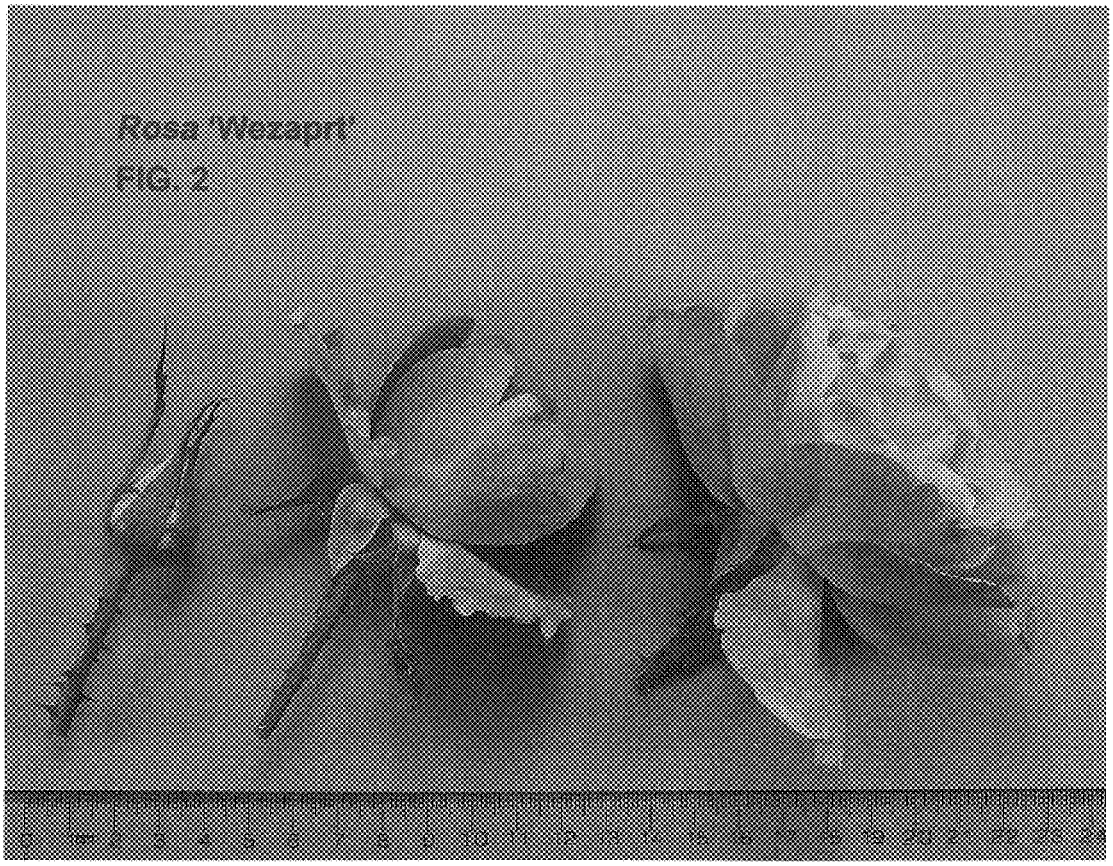
Figure 3:
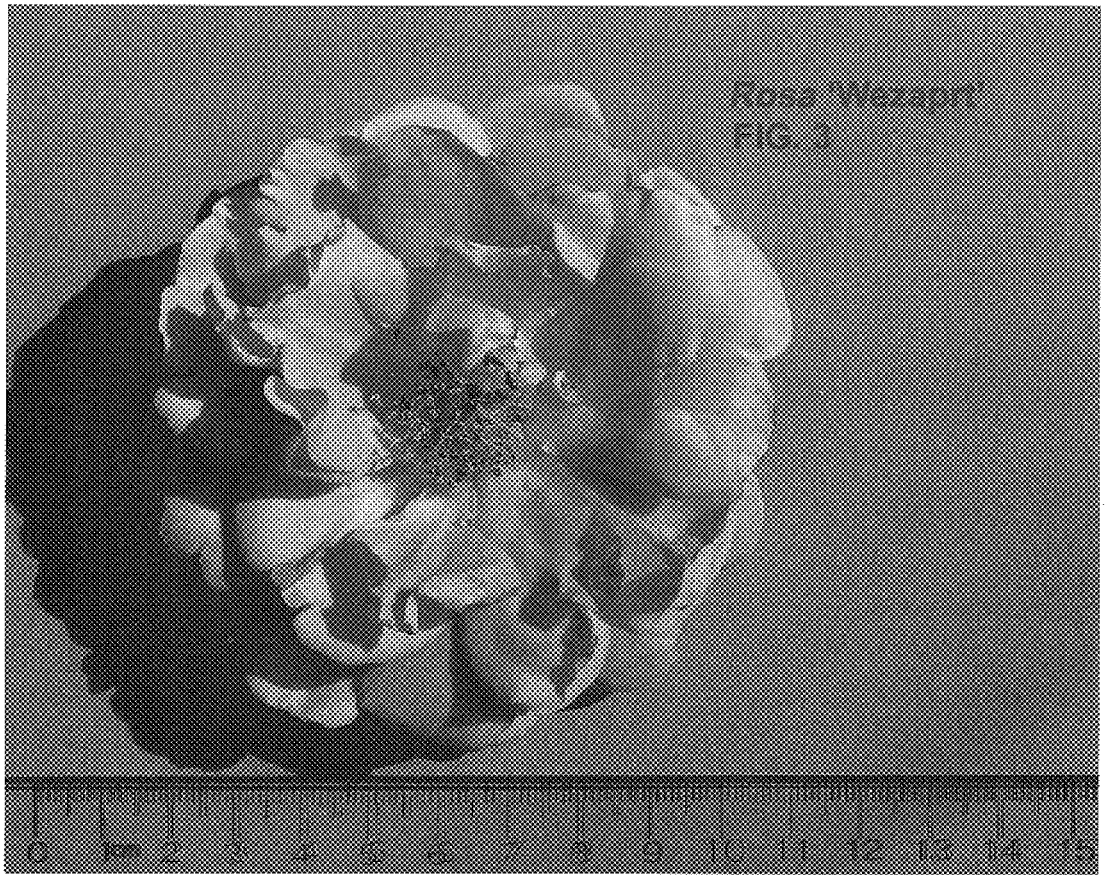
Figure 4:
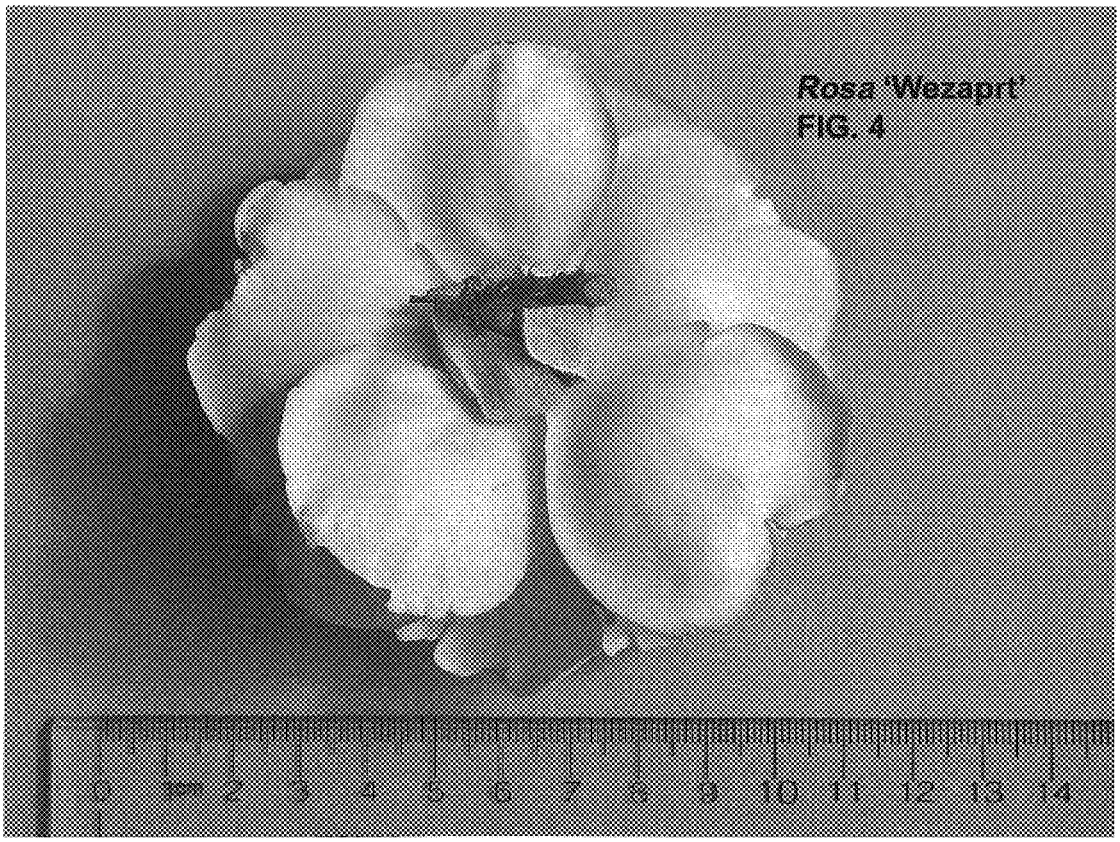
Figure 5:
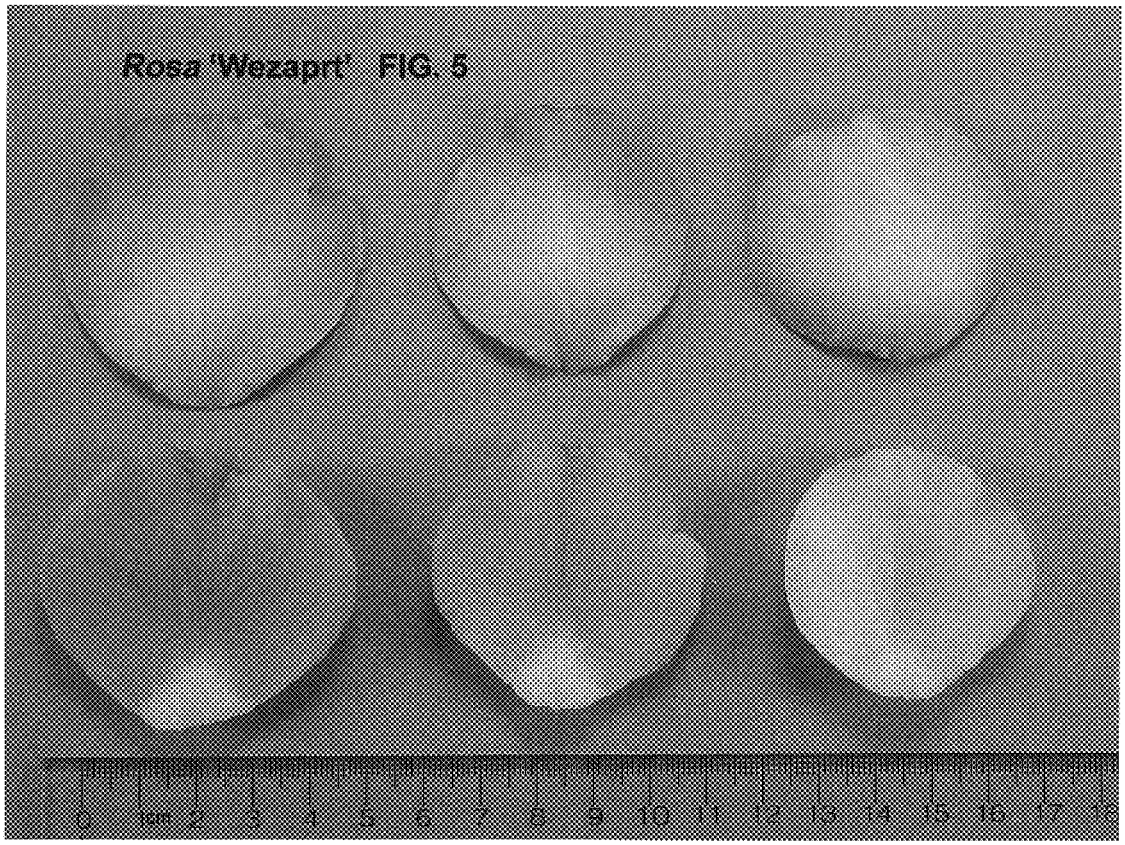
Figure 6:
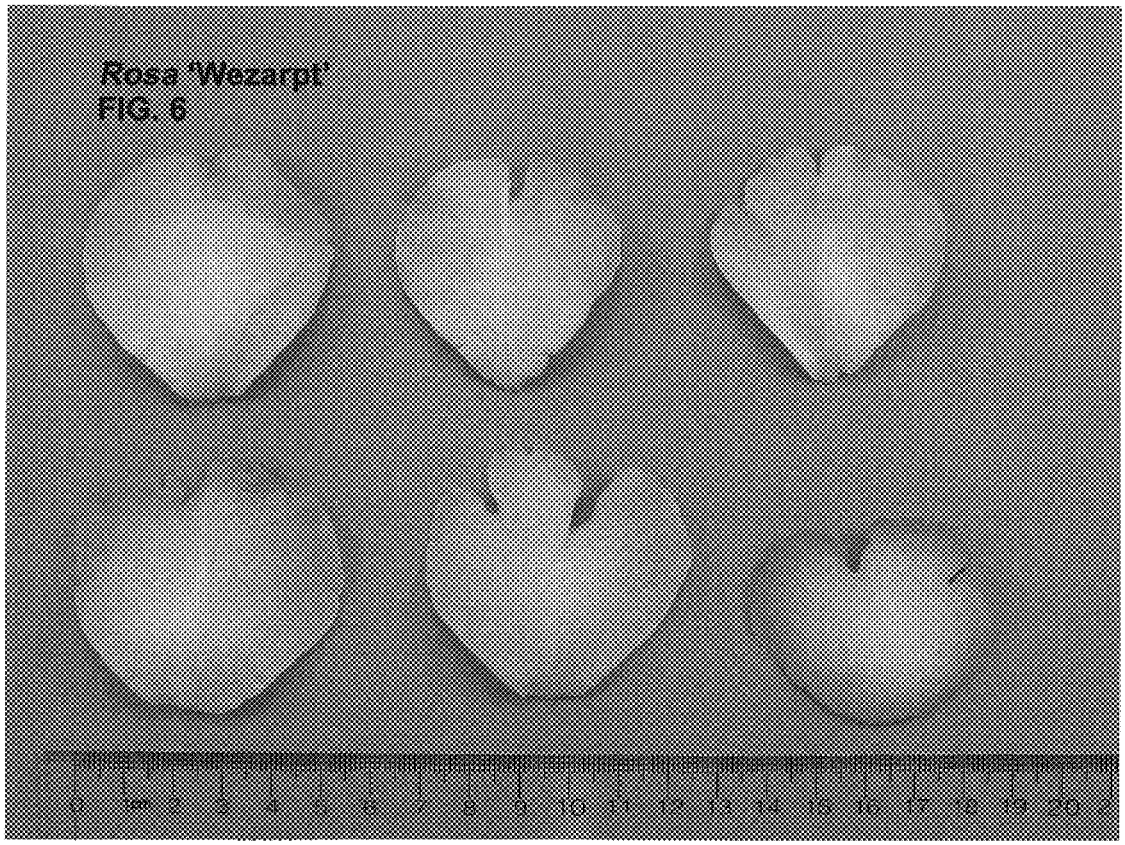
Figure 7:
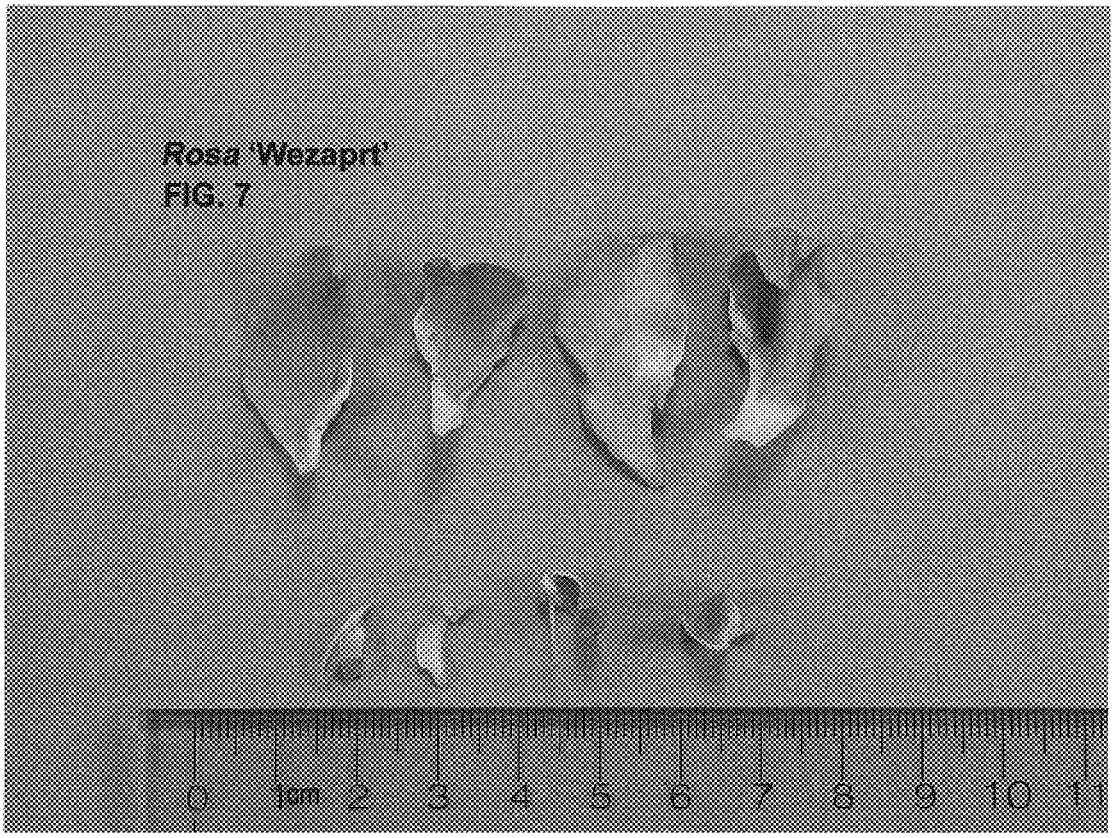
Figure 8:
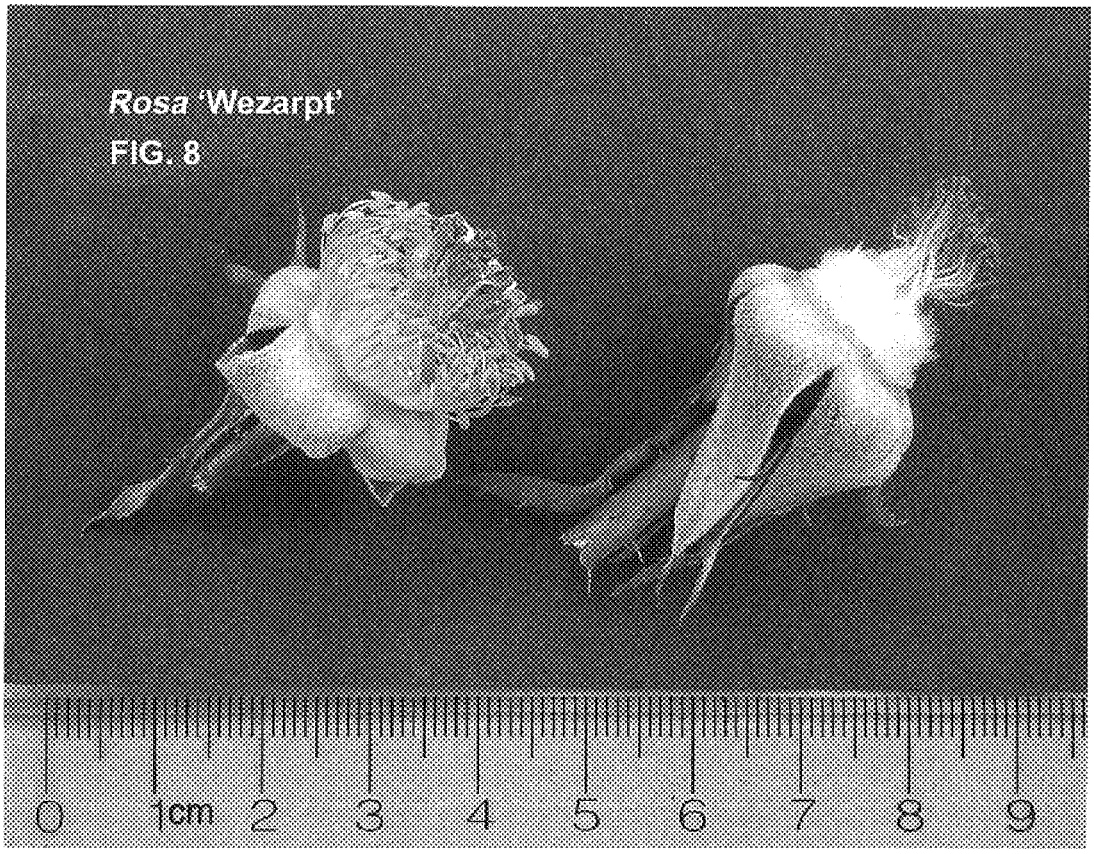
Figure 9:
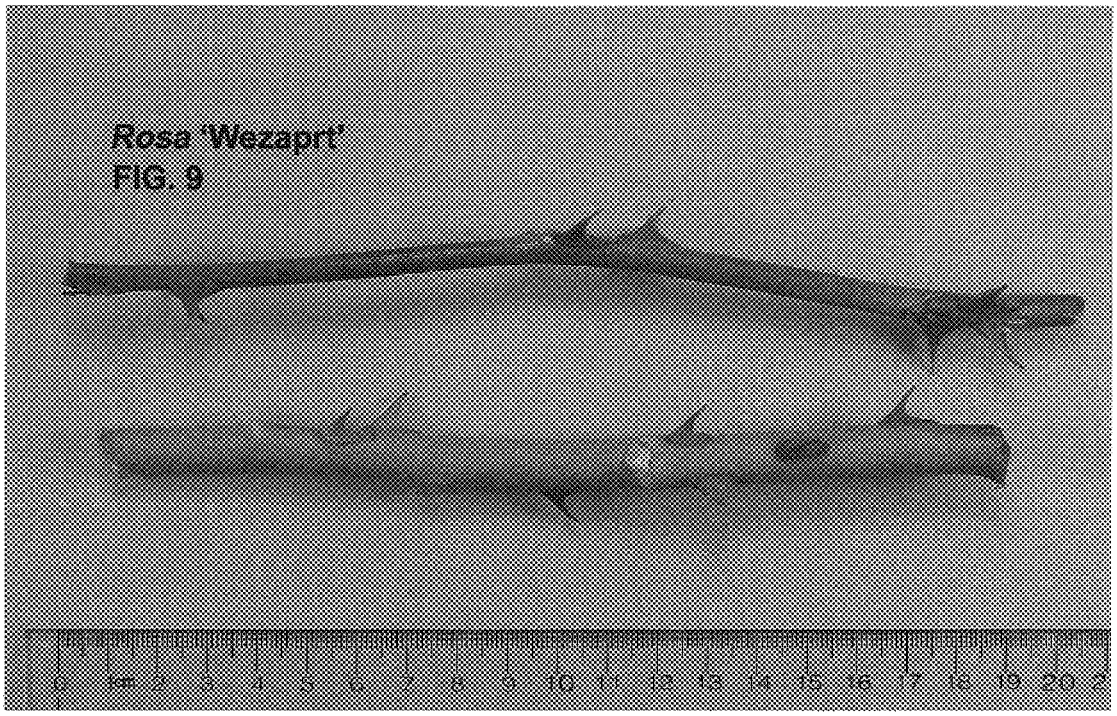
Figure 10:
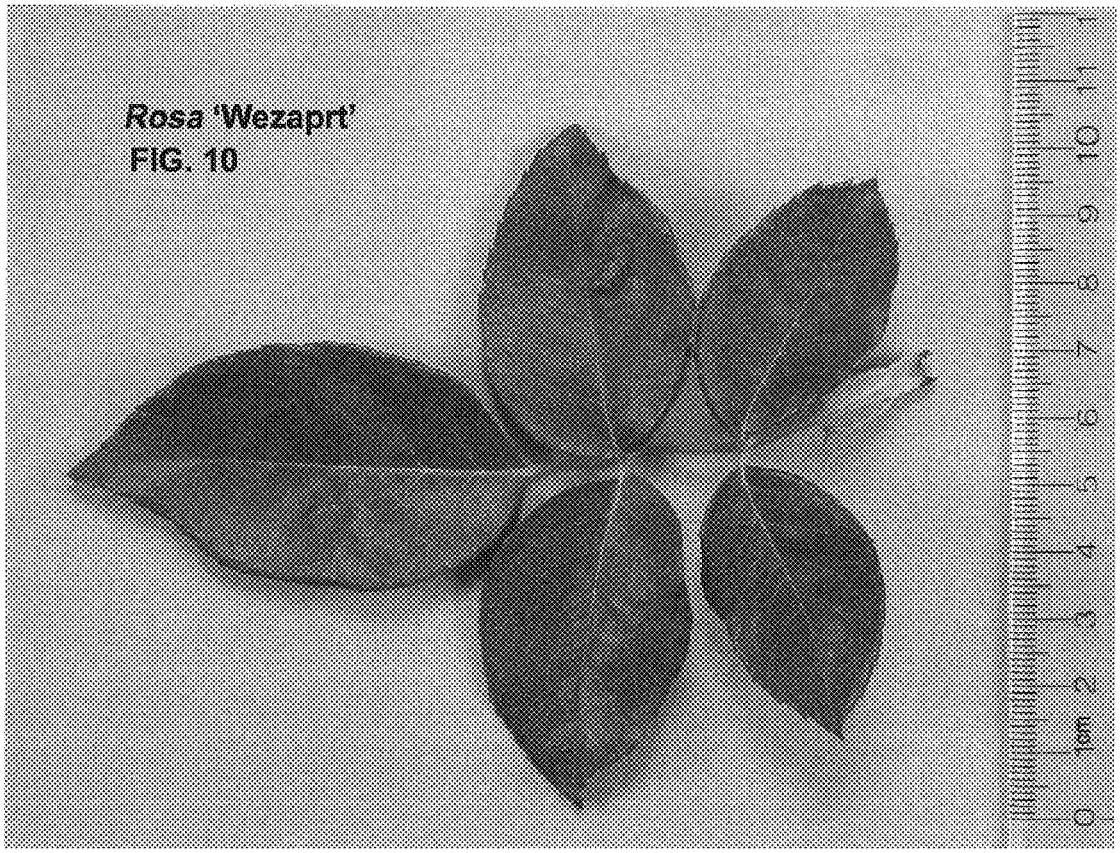
Figure 11:
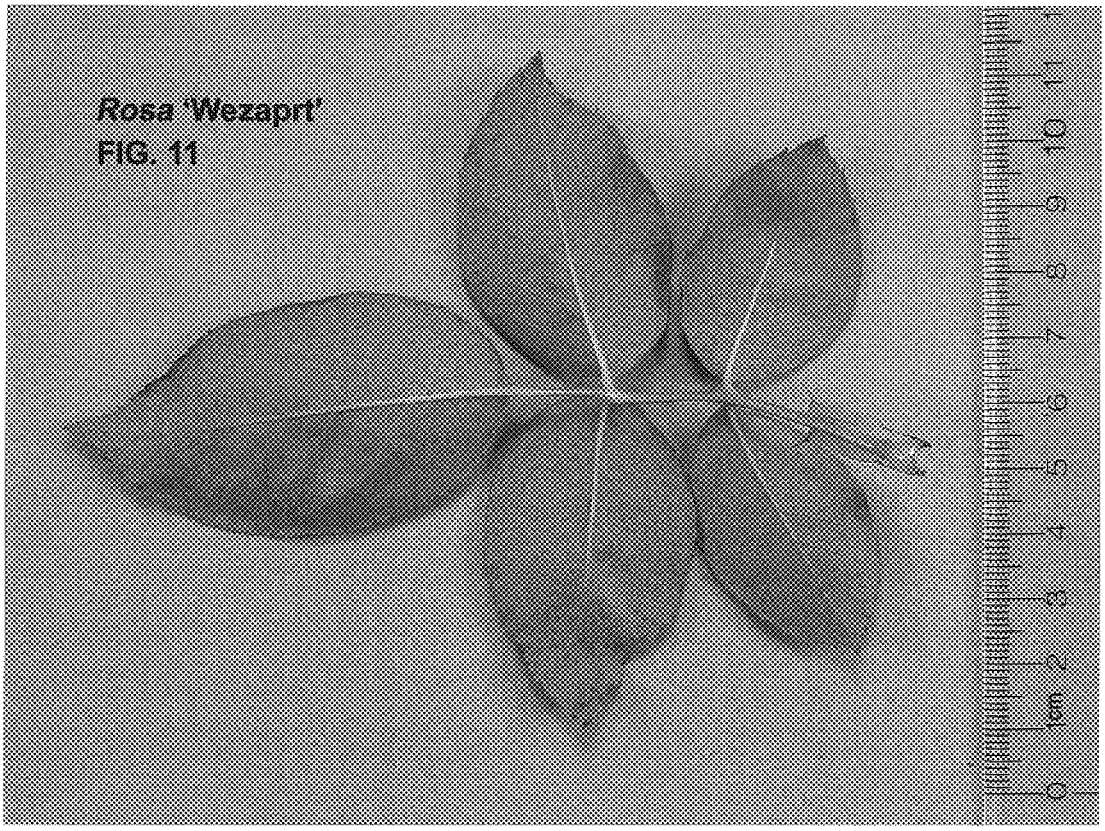

FIG. 1—illustrates a specimen of a young shoot bearing an unopened flower bud;

FIG. 2—illustrates specimens of a floral bud and flowers as they open with a bud at sepal crack at the left, a partly opened flower at the middle, and a fully opened flower at the right;

FIG. 3—illustrates a specimen of a fully opened flower—plan view—obverse;

FIG. 4—illustrates a specimen of a fully opened flower—plan view—reverse;

FIG. 5—illustrates specimens of typical petals—plan view—reverse above, and—plan view—reverse below;

FIG. 6—illustrates specimens of petals from the reverse side showing typical margin variations;

FIG. 7—illustrates specimens of the variation in size and shape of typical petaloids;

FIG. 8—illustrates specimens of typical receptacles with stamens being present at the left and the stamens removed at the right;

FIG. 9—illustrates specimens of typical flowering stems with a younger stem section at the top and an older stem section at the bottom;

FIG. 10—illustrates a specimen of a typical five-leaflet leaf—plan view—obverse; and FIG. 11—illustrates a specimen of a typical five-leaflet leaf—plan view—reverse.

DETAILED DESCRIPTION

The chart used in the identification of the colors is that of The Royal Horticultural Society (R.H.S. Colour Chart). The description is based on the observation of two year-old plants during September 2003 while growing on 'Dr. Huey' rootstock at Wasco, Calif.

Class: Hybrid Tea.

Plant:

*Height.*—Approximately 4 feet at the end of the growing season.

*Width.*—Approximately 2 feet at the end of the growing season.

*Habit.*—Bushy, medium to tall.

Branches:

*Color.*—Young stems: Typically near Yellow-Green Group 146C and 146D with highlights of Greyed-Purple Group 184A, 184B, 185C and Red Group 53B. Adult wood: Near Green Group 138A and 143A.

*Diameter.*—Commonly approximately 11 to 12 mm on average.

*Internode length.*—Approximately 4 cm on average on the lower portions of flowering stems and approximately 8 cm on average on upper portions of flowering stems below the inflorescences.

*Prickles.*—Size: approximately 1 cm in length on average. Quantity: Moderately numerous, approximately 20 true thorns on a stem having a length of 30 cm. Color (young stems): Typically near Greyed-Purple Group 185C and 184A near the base, and progressing through Yellow-Green Group 146A, 146B, 146C, and 146D towards the tip. Color (older stems): Some are near Brown Group 200A near the base and lighten progressively through Brown Group 200B and 200C, and Greyed-Orange Group 166A and 165A towards the tip, and others are lighter and are near Greyed-Orange Group 165A at the base and further lighter progressively through Greyed-Orange Group 165B and 164A and occasionally to 163B and Greyed-Yellow Group 162A and 162B towards the tip. Shape: Hooked.

Leaves:

*Stipules.*—Adnate, pectinate, narrow, triangular, near Yellow-Green Group 144A and 144B in coloration on both surfaces, and with auricle facing outwards. The stipules for a three-leaflet leaf commonly are approximately 12 to 28 mm (average approximately 17.5 mm) in length, and approximately 6 to 8 mm (average approximately 7.1 mm) in width. The stipules for five- and seven-leaflet leaves commonly are approximately 18 to 35 mm (average approximately 24 mm) in length, and approximately 6 to 10 mm (average approximately 7.8 mm) in width.

*Petioles.*—Upper surface: Near Green Group 137A and 137B. Under surface: Yellow-Green Group 144A and 144B. Length: Commonly approximately 19 to 38 mm (approximately 28 mm on average). Diameter: Commonly approximately 1.5 to 2 mm (approximately 1.8 mm on average).

*Size.*—A typical mature three-leaflet leaf commonly is approximately 11 to 12.5 cm (approximately 11.5 cm on average) in length and approximately 9.5 to 11.5 cm (approximately 10.2 cm on average) in width, a typical mature five-leaflet leaf commonly is approximately 12 to 15.5 cm (approximately 13.5 cm on average) in length and approximately 9.5 to 13 cm (approximately 11 cm on average) in width, a typical mature seven-leaflet leaf commonly is approximately 14 to 17 cm (approximately 15 cm on average) in length and approximately 11.5 to 12 cm (approximately 11.9 cm on average) in width.

*Arrangement.*—Alternate and odd-pinnately compound.

*Leaflets.*—Number: 3, 5, and 7. Shape: Typically narrowly to broadly elliptical to occasionally broadly ovate. Apex: Abruptly to somewhat broadly acuminate. Base: Typically moderately broad to narrowly rounded to cuneate to oblique. Size: A terminal leaflet of a mature three-leaflet leaf commonly is approximately 68 mm in length on average and approximately 45 mm in width on average, a terminal leaflet of a mature five-leaflet leaf commonly is approximately 68 mm in length on average and approximately 41 mm in width on average, and a terminal leaflet of a mature seven-leaflet leaf commonly is approximately 72 mm in length on average and approximately 45 mm in width on average. Serration: Serrulate to rarely serrate. Texture: Coriaceus (leathery), and glabrous on the upper and under surfaces. General appearance: Medium green, and with a semi-glossy finish. Venation: Pinnate. Color (young foliage): Upper surface: Combination of Green Group 137A and Yellow-Green Group 147A with Greyed-Purple Group 184A and 184B. Under surface: Near Yellow-Green Group 147B with Greyed-Purple Group 184B and 184C. The mid-rib and smaller veins are near Greyed-Purple Group 184B and 184C. Color (adult foliage): Upper surface: Green Group 137A and 139A. Under surface:

Near Greyed-Green Group 191A with Green Group 137C and Yellow-Green Group 147B. Vein coloration: Near Yellow-Green Group 144A on the upper surface, and near Yellow-Green Group 144A and 144B on the under surface.

Inflorescence:

*Number of flowers.*—Usually one to three flowers per stem.

*Peduncle.*—Yellow-Green Group 143A, 143B, and 143C in coloration, the surface texture is aculeatus (prickly) and commonly bears approximately 20 to 30 prickles of 2 to 4 mm (occasionally up to 6 mm) in length that are near Greyed-Purple Group 185B and near and through Greyed-Red Group 182B and 182C, and Red Group 51C, 54C, 51D and 54D in coloration, the peduncle length typically is approximately 35 to 75 mm (approximately 53.5 mm on average, and the peduncle diameter typically is approximately 3 to 4.5 mm (approximately 3.8 mm on average).

*Sepals.*—Upper surface: Near Green Group 137B and 137C with some lightening towards Yellow-Green Group 143A, 143B, and 144A. Under surface: Near Yellow-Green Group 144A with lightening towards Yellow-Green Group 144C and some Yellow-Green Group 143A and 143B. Shape: Lanceolate with a few foliaceous extensions on 2 or 3 sepals. Number: 5. Size: Typically approximately 22 to 25 mm (average approximately 35 mm) in length and approximately 4.5 to 12.5 mm (average approximately 11 mm) in width.

*Buds.*—Shape: Globular. Size: Large. Length: Approximately 3.5 cm on average. Diameter: Approximately 19.5 mm at first sepal crack. Color upon opening: Upper surface: Yellow Group 9A. Under surface: Combination of Orange-Red Group 32A and 33A.

*Flower.*—Shape: Double and cup-like. Diameter: Large, and commonly approximately 8 to 11 cm when fully open and approximately 9 cm on average. Petal length: Typically approximately 37 to 63 mm and approximately 49 mm on average. Petal width: Typically approximately 36 to 59 mm and approximately 48 mm on average. Petal texture: Typically glabrous, coriaceus, and commonly thicker than most rose petals. Petal margin: Entire at the base and occasionally slightly crimped with the outer petals typically being revolute, and the inner petals typically being repand with the innermost petals becoming sinuate. Petal apex: Variable ranging from broadly obtuse to truncate, emarginate, praemorsus to tridentatus. Petal base: Broadly rounded to broadly cuneate to cuneate. Petal vein pattern: Actinodromous. Color (when opening begins): Upper surface: Near Yellow Group 12A and 13A at the base and shading towards Yellow-Orange Group 15A with highlights of Orange-Red Group 32A and 33B approaching the edges. Under surface: Near Yellow Group 12A and 13A at the base and shading towards Orange Group 25A with highlights of Orange-Red Group 32A and 33B approaching the edges. Color (when blooming): Upper surface: Near Yellow Group 12A and 13A at the base with highlights of Orange Group 24A, 25A, 25B, 26A, 26B and 26C approaching the edges. Under surface: Near Yellow Group 12A and 13A at the base shading near and through Orange Group 29A and 29B and Orange-Red Group 32B, 33B and 33C, and near Greyed-Orange Group 170D and 171D approaching the edges. Color (at end of opening): Upper surface: Near Yellow Group 12A, 12B and 13A at the base shading near and through Yellow-Orange Group 16C, 16D, 15D, 19B and 19C approaching the edges. Under surface: Near Yellow Group 12A, 12B and 12C at the base shading near and through Yellow-Orange Group 16C, 16D, and 15D with some Orange-Red Group 33D and Greyed-Orange Group 170D approaching the edges. Petal vein coloration: On the upper surface the veins are near Orange Group 25A, 26A, and 28A. Fragrance: Strongly spicy. Petal shape: Sub-orbicular to occasionally orbicular or broadly obovate especially for the innermost petals. Petal number: Commonly ranges from approximately 19 to 26 under typical growing conditions with an average of approximately 22. Petal arrangement: Rosulate. Petaloids: Commonly present, and typically number approximately 1 to 8 per flower with the average number being approximately 4, the sizes shapes vary greatly as illustrated in FIG. 7, and the coloration is substantially the same as that of the petals at the same stage of development. Petal drop: The petals commonly detach cleanly. Lasting quality: A typical flower commonly lasts approximately 6 to 10 days when cut and place in a vase. Stamen number: Commonly approximately 110 to 155. Anthers: Approximately 2.1 to 3.1 mm (approximately 2.5 mm on average) in length, and near Yellow-Orange Group 17A, 17B and 22A in coloration. Filaments: The length varies widely and commonly ranges from approximately 4 to over 15 mm, the diameter commonly is approximately 0.3 mm, and the coloration commonly is near Yellow-Orange Group 14A and 14B. Pollen: Present and near Yellow-Orange Group 17A and 17B in coloration. Pistils: Commonly approximately 70 to 140 per bloom. Stigmas: Approximately 0.7 to 1 mm in size (approximately 0.87 on average) when the flower is fully open, and the coloration is near Greyed-Orange Group 163A at the center and near Yellow-Orange Group 22A toward the edges. Styles: Approximately 9.7 to 12.7 mm in length (approximately 10.7 mm on average), approximately 0.3 mm in diameter, and the coloration when the flower is fully open is near Red Group 47A and 47B with Red Group 43D, 44A, 48A, and 48C, and nearer the base Yellow-Orange Group 18A, 18B, and 18C. Receptacle: Generally shallow and flattened in configuration, possesses a glaucous surface, approximately 5 to 7 mm in length at full bloom, approximately 10 to 12 mm in diameter at full bloom, and near Yellow-Green Group 144A and 144B in coloration. Hips: None observed during observation to date.

Development:

*Vegetation.*—Vigorous and uniform.

*Blooming.*—Mostly single blooms and sometimes in clusters.

*Hardiness.*—U.S.D.A. Hardiness Zone No. 7.

*Tolerance to diseases.*—Good with respect to rose black spot (*Marssonia rosae*).

*Tolerance to drought.*—None.

The new 'Wezaprt' variety has not been observed under all possible environmental conditions to date. Accordingly, it is possible that the phenotypic expression may vary somewhat with changes in light intensity and duration, cultural practices, and other environmental changes without a variance of the genotype.

I claim:

1. A new and distinct variety of Hybrid Tea rose plant characterized by the following combination of characteristics:

(a) exhibits a bushy, vigorous and uniform growth habit, (b) forms attractive large double blossoms with a spicy fragrance that are amber-orange in coloration, (c) forms medium green semi-glossy foliage that contrasts well with the lighter-colored blossoms, (d) exhibits good disease tolerance to rose black spot, and (e) is particularly well suited for growing as attractive ornamentation;

substantially as herein shown and described.

* * * * *

*Rosa* 'Wezaprt'

Rosa 'Wezaprt'

Rose 'Wezaprel'

Rosa 'Wezaprt'

Rosa 'Wezaprt' FIG. 5

Rosa 'Wezarpt'

*Rosa* 'Wezaprl'

0
1cm
2
3
4
5
6
7
8
9
10
11

Rosa 'Wezarpt'

0
1cm
2
3
4
5
6
7
8
9

Rosa 'Wezaprt'

Rosa 'Wezaprt'

1cm

Rosa 'Wezaprt' cm
0
1
2
3
4
5
6
7
8
9
10
11
12